United States Patent [19]
Herring

[11] Patent Number: 5,308,459
[45] Date of Patent: May 3, 1994

[54] BIOSYNTHETIC CEREBROSPINAL FLUID CONTROL AND METHOD OF USE

[75] Inventor: Kathryn D. Herring, Miami, Fla.

[73] Assignee: Baxter Diagnostics Inc., Deerfield, Ill.

[21] Appl. No.: 965,653

[22] Filed: Oct. 23, 1992

Related U.S. Application Data

[62] Division of Ser. No. 665,874, Mar. 7, 1991, abandoned.

[51] Int. Cl.⁵ .................. G01N 27/26; G01N 27/447
[52] U.S. Cl. ............................. 204/180.1; 204/182.8
[58] Field of Search ............ 204/299 R, 182.8, 180.1, 204/182.7

[56] References Cited

U.S. PATENT DOCUMENTS 4,874,694 10/1989 Gandy et al. ............... 204/182.8 X
4,892,814 1/1990 Harrington et al. ......... 204/182.8 X

FOREIGN PATENT DOCUMENTS 2439017 5/1980 France .
50-82224 7/1975 Japan .

Primary Examiner—John Niebling
Assistant Examiner—John S. Starsiak, Jr.
Attorney, Agent, or Firm—Louise S. Pearson; Michael P. Bucklo; Susan Bennett Fentress

[57] ABSTRACT

The present invention relates to a biosynthetic cerebrospinal fluid control and method of use. Additionally, this invention relates to the isolation and purification of stable liquid human prealbumin, a component in the biosynthetic cerebrospinal fluid control.

2 Claims, 6 Drawing Sheets

| FRACTION | % |
|---|---|
| Prealbumin | 4.6 |
| Albumin | 58.3 |
| Alpha 1 | 3.6 |
| Alpha 2 | 7.1 |
| Beta | 11.0 |
| Gamma | 15.3 | though this is specific to the biosynthetic fluid itself, the description of each individual process.

BIOSYNTHETIC CEREBROSPINAL FLUID CONTROL AND METHOD OF USE

This is a division of application Ser. No. 07/665,874, filed on Mar. 7, 1991 now abandoned.

BACKGROUND OF THE INVENTION

1. Field of the Invention

This invention relates to a stable biosynthetic liquid cerebrospinal fluid control and method of use. Additionally, this invention relates to the isolation and purification of stable liquid human prealbumin, a component in the biosynthetic cerebrospinal fluid control.

2. Description of Related Art

Cerebrospinal fluid is formed by an ultrafiltration of the plasma. Normal values for cerebrospinal fluid analytes are not the same as plasma values. This difference is a result of the filtration process being selective and the fact that the chemical composition is adjusted by the blood-brain barrier. Analysis of this chemical composition is an important diagnostic procedure. Disease increases cerebrospinal fluid protein concentrations. Elevated cerebrospinal fluid total protein is an indicator of central nervous system pathology such as damage to the blood-brain barrier caused by meningitis or hemorrhage. IgG is the primary immunoglobulin of cerebrospinal fluid. It is increased in several neurological conditions such as multiple sclerosis and viral meningoencephalitis. Analysis of cerebrospinal fluid by serum protein electrophoresis is an important diagnostic test in the diagnosis of multiple sclerosis. Low glucose values signal infections such as bacterial, tuberculous or fungal meningitis. Low values are also seen as a result of infiltration of the meninges with malignant cells. High lactic acid levels in cerebrospinal fluid indicate bacterial or tuberculous infection and rule out viral meningitis. Low cerebrospinal fluid chloride levels can be used as an indicator of tuberculous meningitis.

Since the chemical composition of cerebrospinal fluid is similar to plasma comparable tests are performed. However, the levels of these constituents are not the same resulting in different normal values than those used for plasma. In order to assess the accuracy and precision of these diagnostic tests, a control similar to cerebrospinal fluid must be run. In the case of serum protein electrophoresis, a known protein control is always run in a separate well. The protein fractions in cerebrospinal fluid are not always clearly detected. Therefore, a control in which all the serum protein fractions are clearly defined is important. Most cerebrospinal fluid controls are prepared from actual spinal fluid. There are no tests, however, to detect the presence of infectious diseases in spinal fluid. Additionally, the recovery of spinal fluid is difficult and expensive and the quality is varied. Other cerebrospinal fluid controls have been made from normal human blood serum diluted with a diluent containing glucose and chloride ions, and then lyopholized. Reconstitution of the control is then required before it can be used. See U.S. Pat. No. 3,753,925.

SUMMARY OF THE INVENTION

The present invention relates to biosynthetic cerebrospinal liquid controls based on human serum spiked with prealbumin. Two controls are disclosed: one simulating normal spinal fluid and the second simulating abnormal spinal fluid. The product is prepared from human serum and purified human prealbumin in a buffer matrix formulated to simulate human cerebrospinal fluid. In particular, this invention relates to a stable liquid human based cerebrospinal fluid control made by the process comprising: (a) combining a sufficient amount of lactic acid, chloride, glucose, serum, purified prealbumin, and potassium in a buffer to simulate normal human cerebrospinal fluid; (b) gassing said filtered fluid with oxygen to obtain normal electrophoretic pattern for human cerebrospinal fluid, and (c) filtering said fluid to remove all microbial contaminants.

The present invention also relates to high purity prealbumin and a process to make prealbumin. In particular, this invention relates to a purified prealbumin made by the process comprising: (a) diluting human serum with a first buffer; (b) extracting globulins, ceroplasm and albumin from normal serum diluted in a first buffer using ion exchange chromatography; (c) isolating the prealbumin containing fractions eluded from Step (b) by immunodiffusion; (d) pooling, concentrating and buffer exchanging the prealbumin containing fractions of Step (c) with a second buffer; (e) removing albumin from the said prealbumin containing pooled fractions of Step (d) by affinity chromatography; (f) isolating the prealbumin containing fractions eluted from Step (e) by immunodiffusion; (g) pooling and concentrating and buffer exchanging said prealbumin containing fractions of Step (f) with a third buffer to increase the prealbumin concentration; (h) removing globulins from said pooled fractions of Step (g) by ion exchange chromatography; (i) pooling, concentrating and buffer exchanging with a fourth buffer to increase prealbumin concentrations; (j) purifying the prealbumin containing fractions of Step (i) by gel filtration to remove any residual proteins; (k) isolating purified prealbumin fractions from Step (j) by electrophoresis and immunodiffusion; and (l) pooling, concentrating and sterile filtering said purified prealbumin fractions of Step (k).

DETAILED DESCRIPTION OF THE INVENTION

Figure 1:
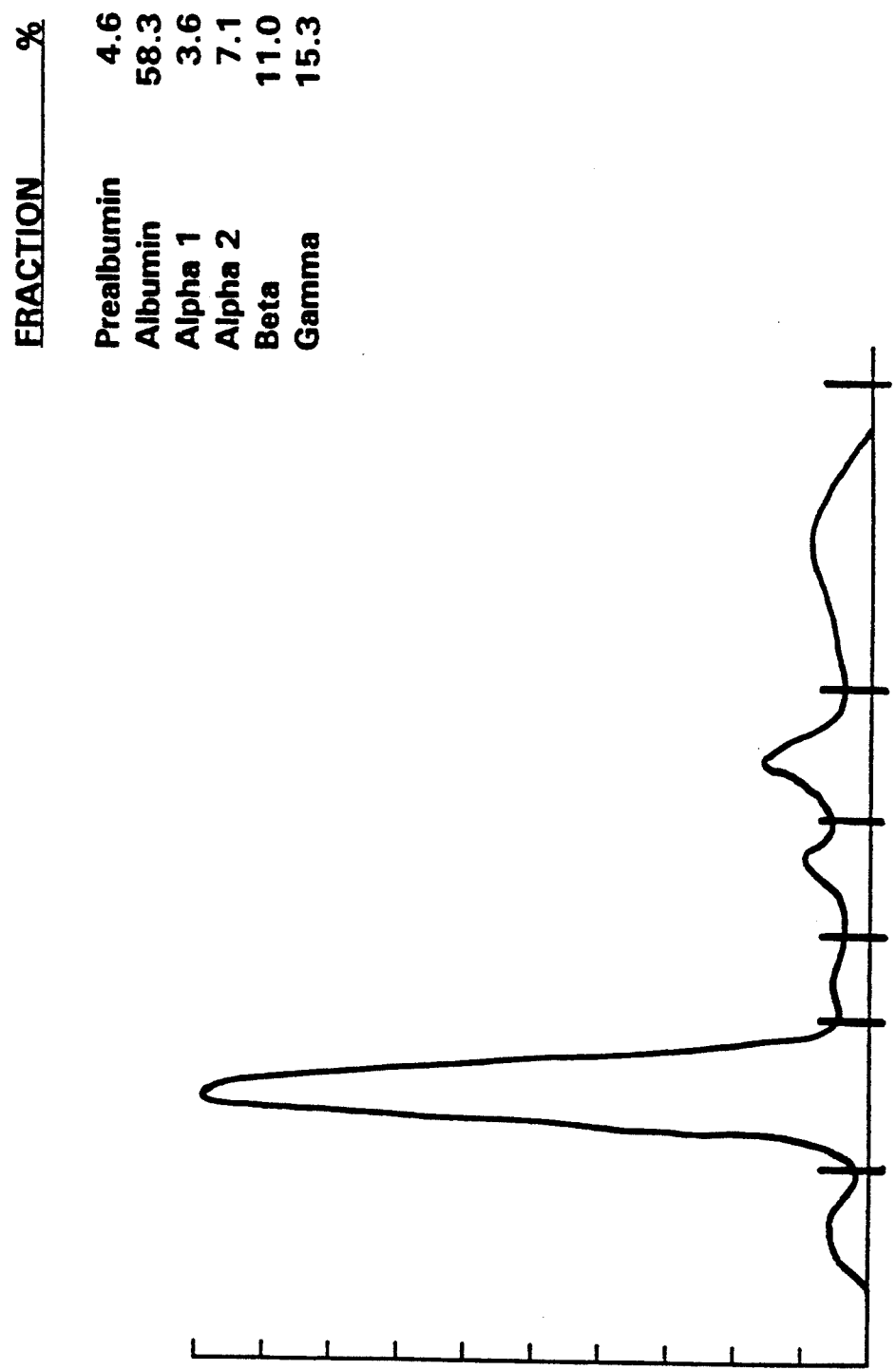
FIG. 1 shows protein electrophoresis of cerebrospinal fluid prepared according to this method.

The disclosed invention involves diluting human serum with constituents adjusted within ranges for cerebrospinal fluid. Cerebrospinal fluid contains a very small amount of protein as compared to serum. The protein fractions are similar to those found in serum; however, for serum the quantity of prealbumin present is less than 1% whereas the quantity present in cerebrospinal fluid is 2 to 7% of the total proteins. In order to increase the level of this protein, a prealbumin spike was added. This protein was effectively isolated from human serum using column chromatography.

The product is formulated by the addition of the required constituents to a 50 to 80 mM HEPES buffer matrix. The pH of the buffered matrix is 7.3. Serum and prealbumin are added to the specifications required for each level. Glucose, lactic acid, chloride, sodium, potassium are added to obtain the desired concentrations as specified in Table I. The buffered solution is then gassed with 100% oxygen to remove a pre-albumin fraction that migrates faster than prealbumin and then sterile filtered.

The assayed constituents for this product are: protein, glucose, lactic acid, chloride, sodium, potassium, immunoglobulins and protein fractions by electrophoresis.

The Level I represents normal spinal fluid. Level II represents abnormal spinal fluid. The conditions observed in both levels of the control are most commonly seen in meningitis, multiple sclerosis, and brain trauma or injuries.

TABLE I

Constituent Targets:

| PARAMETER | NORMAL | LEVEL I | LEVEL II | UNITS |
|---|---|---|---|---|
| Sodium | 139–150 | 140–160 | 120–140 | mmol/L |
| Potassium | 2.7–3.9 | 2–4 | 3–6 | mmol/L |
| Chloride | 116–127 | 110–130 | 90–110 | mmol/L |
| Lactic Acid | 1.1–2.8 | 1–3 | 7–9 | mmol/L |
| Glucose | 45–80 | 45–80 | 25–40 | mg/dL |
| Protein | 15–45 | 15–45 | 50–80 | mg/dL |
| ELECTROPHORETIC SEPARATION (% of Total Protein) | | | | |
| PREALBUMIN | 2–7 | 2–7 | 2–7 | % |
| ALBUMIN | 56–76 | 45–76 | 45–76 | % |
| GLOBULINS: | | | | |
| ALPHA 1 | 2–7 | 2–7 | 2–7 | % |
| BETA | 7–18 | 7–18 | 7–18 | % |
| GAMMA | 7–14 | 7–19 | 7–19 | % |
| IMMUNOGLOBULINS (RID) | | | | |
| IgA | 0–0.2 | trace | trace | mg/dL |
| IgG | 10–40 | 0–15 | 5–40 | mg/dL |
| IgM | 0–0.6 | trace | trace | mg/dL |

Microbiology Specs: No growth to USP procedures.

EXAMPLE 1

Prealbumin Isolation from Serum

Units of normal human serum were pooled and the volume measured to be approximately two liters. The pooled serum was diluted 50% in 50 mM potassium phosphate buffer, pH 7.5, 0.1% azide. The diluted serum was sterile filtered through a 0.22 micron filter into sterile containers. The prepared serum was then loaded on to an ion exchange column containing DEAE Sephacel TM or DEAE Sepharose TM (Pharmacia) that has been previously equilibrated with 50 mM potassium phosphate buffer, pH 7.5, 0.1% azide. After completion of the sample load, the column was washed with 50 mM potassium phosphate buffer, pH 7.5, 0.1% azide until an OD at 280 nm is less than 0.2 as measured on an UV spectrophotometer. The bound proteins were eluted with a gradient from 0 to 1M NaCl in 0.5M potassium phosphate buffer, pH 7.5, 0.1% azide. 12 mL fractions were collected until the gradient was exhausted. This column removed ceruloplasmin, globulins and albumin from the sample.

The fractions are tested by immunodiffusion for the presence of prealbumin. When the fractions that contain prealbumin are identified, they are pooled, concentrated, and buffer exchanged with 20 mM potassium phosphate buffer, pH 7.1, 0.02% azide. The pooled fractions were concentrated to a total protein of approximately 4 to 5 g/dL. The fraction pool is then loaded on an affinity column containing Affi Gel Blue TM (BIORAD) or Blue Sepharose TM (Pharmacia) which has been equilibrated with 20 mM phosphate buffer, pH 7.1, 0.02% azide. This chromatography media contains Cibacron Blue Dye F3G-A which has an affinity for albumin. After the sample was loaded, the fraction collector was started and 6 mL fractions were collected as the column was washed with 20 mM phosphate buffer, pH 7.1, 0.02% azide. As the sample was loaded, albumin binds to the blue dye and the remaining proteins passed through the column. The prealbumin containing fractions were pooled, concentrated and buffer exchanged with 50 mM potassium phosphate buffer, pH 7.5, 0.1% azide. The fractions were concentrated to a total protein of approximately 3 to 4 g/dL. The concentrated fractions were then loaded onto an ion exchange column containing DEAE Sephacel TM or DEAE Sepharose TM (Pharmacia) which has been equilibrated with 50 mM potassium phosphate buffer, pH 7.5, 0.1% azide. The proteins were eluted using a salt gradient of 0 to 1M NaCl in 50 mM potassium phosphate buffer, pH 7.5, 0.1% azide. Fractions of 3 mL were collected until the gradient was exhausted. Fractions were tested for the presence of prealbumin using immunodiffusion.

When the prealbumin containing fractions have been identified these fractions were pooled, concentrated and buffer exchanged in 50 mM phosphate buffer with 170 mM sodium chloride, pH 7.5, 0.02% azide. The fraction pool was concentrated to a total protein of approximately 2–7 g/dL. This fraction pool was then loaded on a gel filtration column which contained ULTROGEL® AcA 54 (IBF Biotechnics) equilibrated with 50 mM phosphate buffer with 170 mM sodium chloride, pH 7.5, 0.02% azide. This column was then washed with 50 mM phosphate buffer with 170 mM sodium chloride, pH 7.5, 0.02% azide. Fractions were collected of 3 mL each. Two protein peaks were collected. The prealbumin was mostly contained in the second peak. Fractions were tested for the presence of prealbumin using immunodiffusion. The fractions that contain prealbumin were then tested by serum protein electrophoresis for the presence of other serum proteins. The purified prealbumin fractions were selected, pooled and concentrated to a total protein of approximately 1 to 4 g/dL. These pooled fractions were sterile filtered and stored at 2°–8° C.

Figure 2:
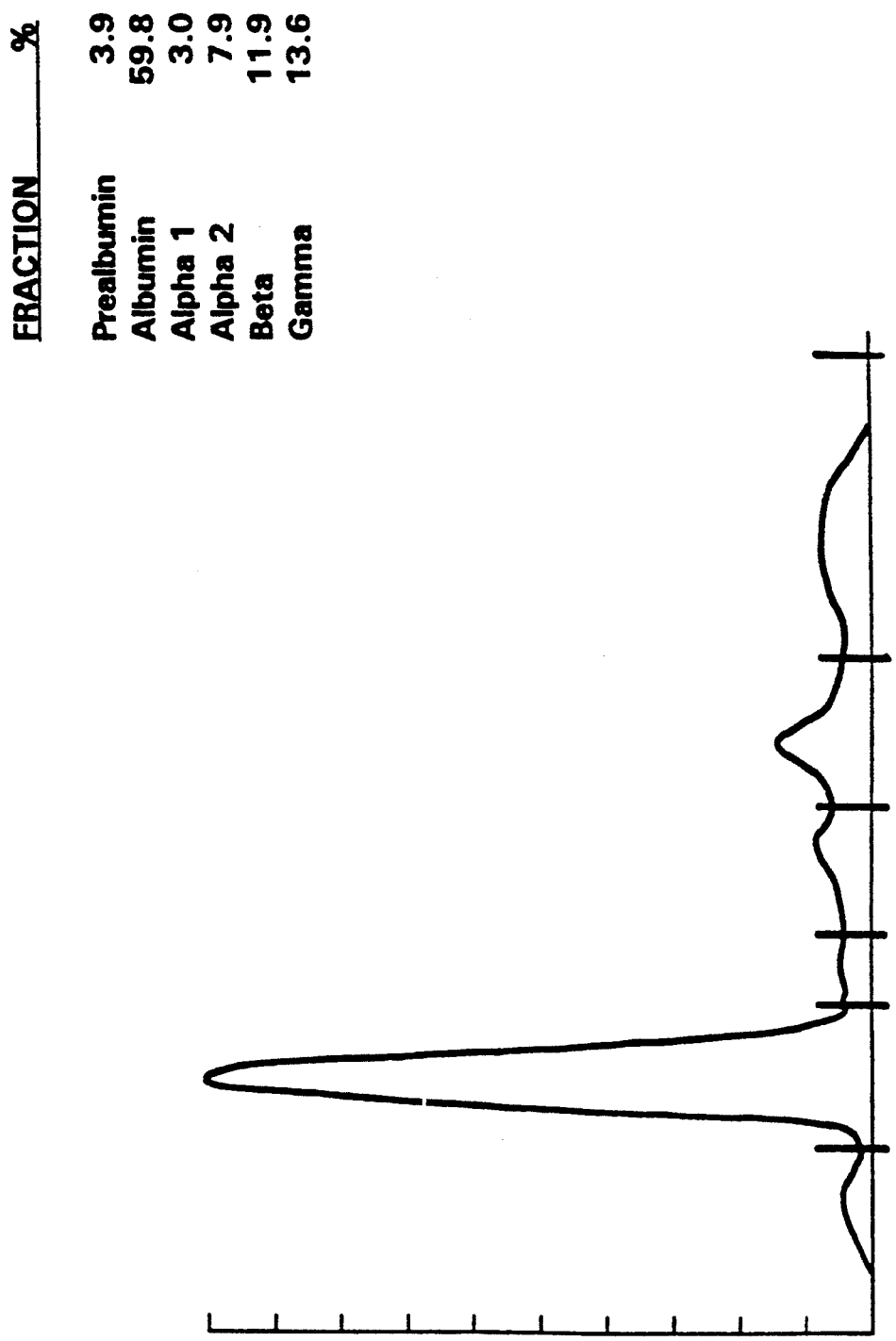
FIG. 2 shows protein electrophoresis of cerebrospinal fluid prepared according to this method.
Figure 3:
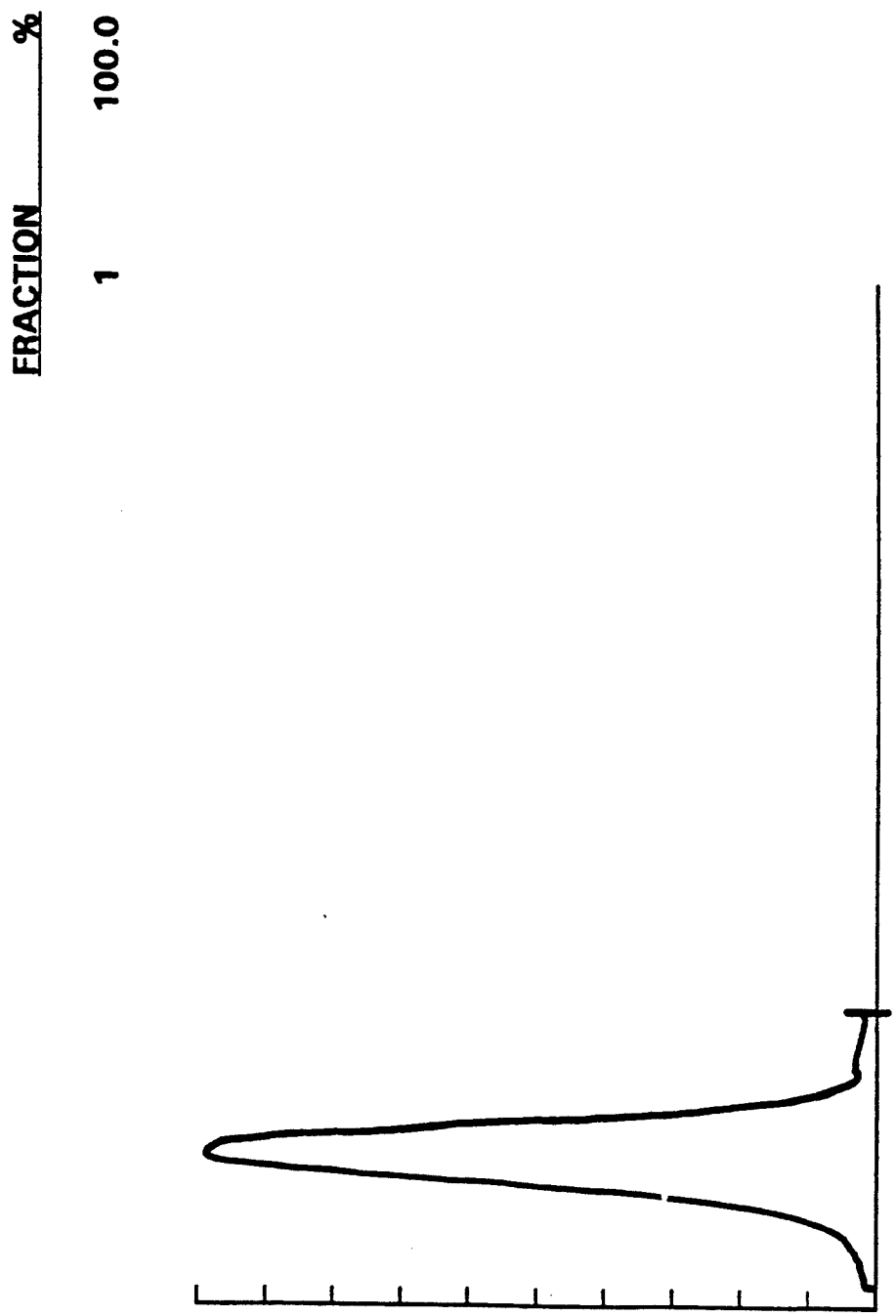
FIG. 3 shows protein electrophoresis of prealbumin prepared by the present method. Analysis by serum protein electrophoresis.
Figure 4:
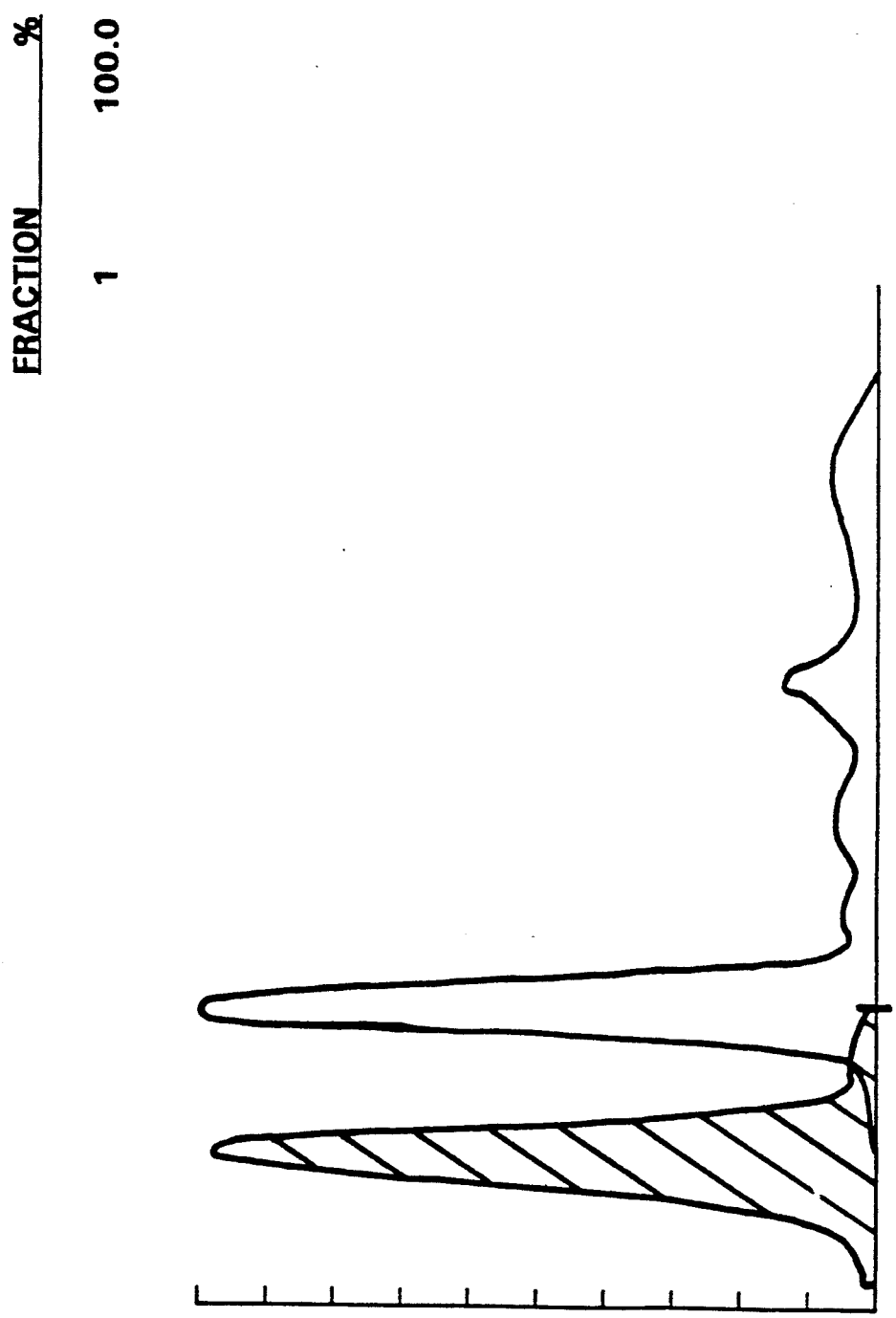
FIG. 4 shows an overlay of protein electrophoresis of prealbumin prepared by the present method, on to normal human serum pattern.

The purified prealbumin was tested for total prealbumin content using serum protein electrophoresis, and radial immunodiffusion analysis for quantitative measurement of prealbumin. A single peak was observed and the prealbumin was found to be 90 to 100% pure by protein electrophoresis. See FIG. 3. When compared to the electrophoretic pattern of normal serum, the peak is observed in the prealbumin region and no other serum proteins are present. See FIG. 4. When spiked into normal serum, the resulting electrophoretic pattern showed a peak in the prealbumin region. See FIG. 1 and 2. SDS PAGE electrophoresis shows a single protein to be present. This protein is found in the correct molecular weight range for prealbumin (54,000) The quantity of prealbumin demonstrated yields of 80 to 100% depending on the purity of prealbumin required. A commercially available prealbumin prepared from human plasma using the method defined by Raz, A., et al., J. Biol. Chem., 244,12 (1969) was evaluated for purity.

Figure 5:
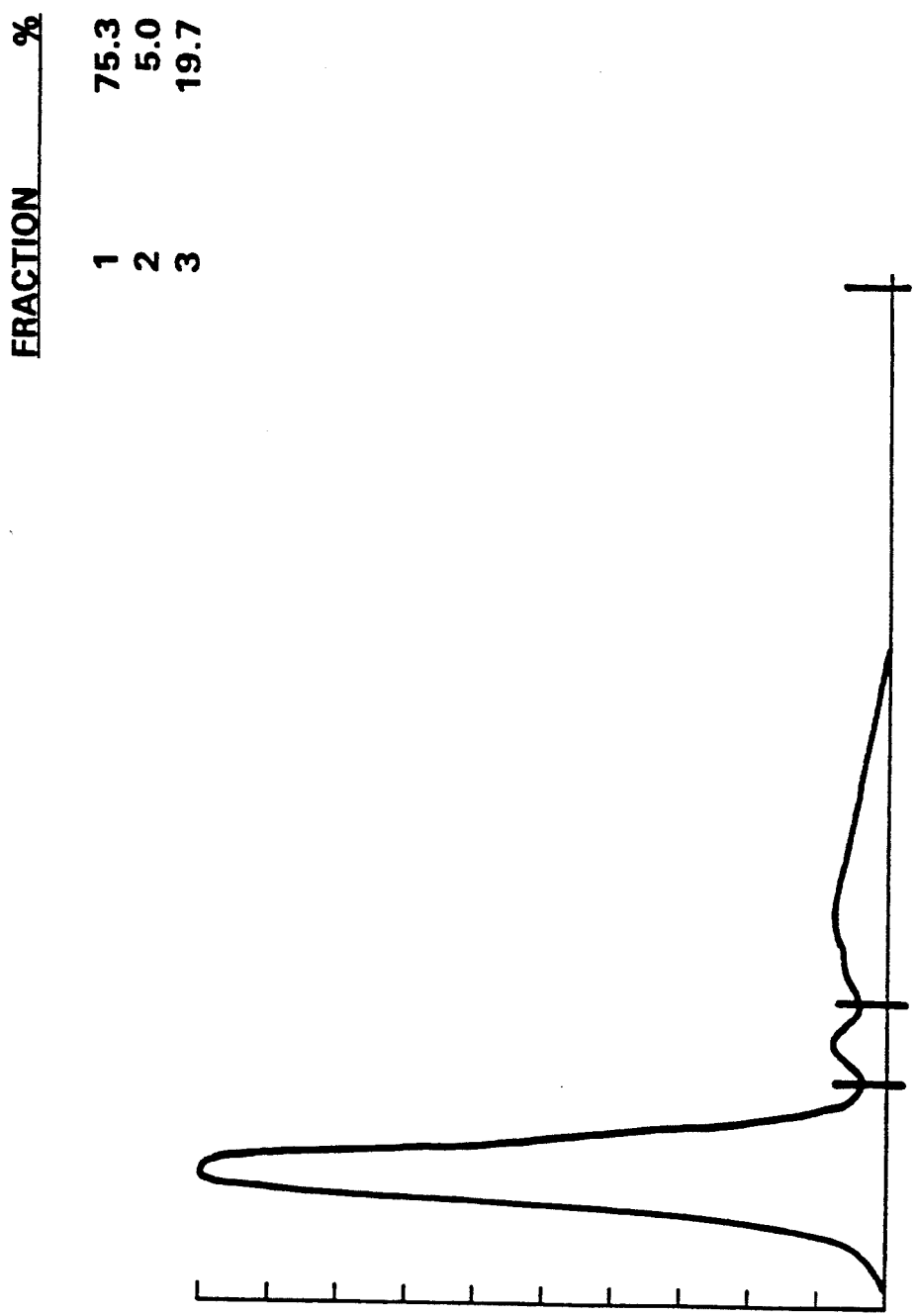
FIG. 5 shows protein electrophoresis of prealbumin prepared by the Raz method; analysis by serum protein electrophoresis.
Figure 6:
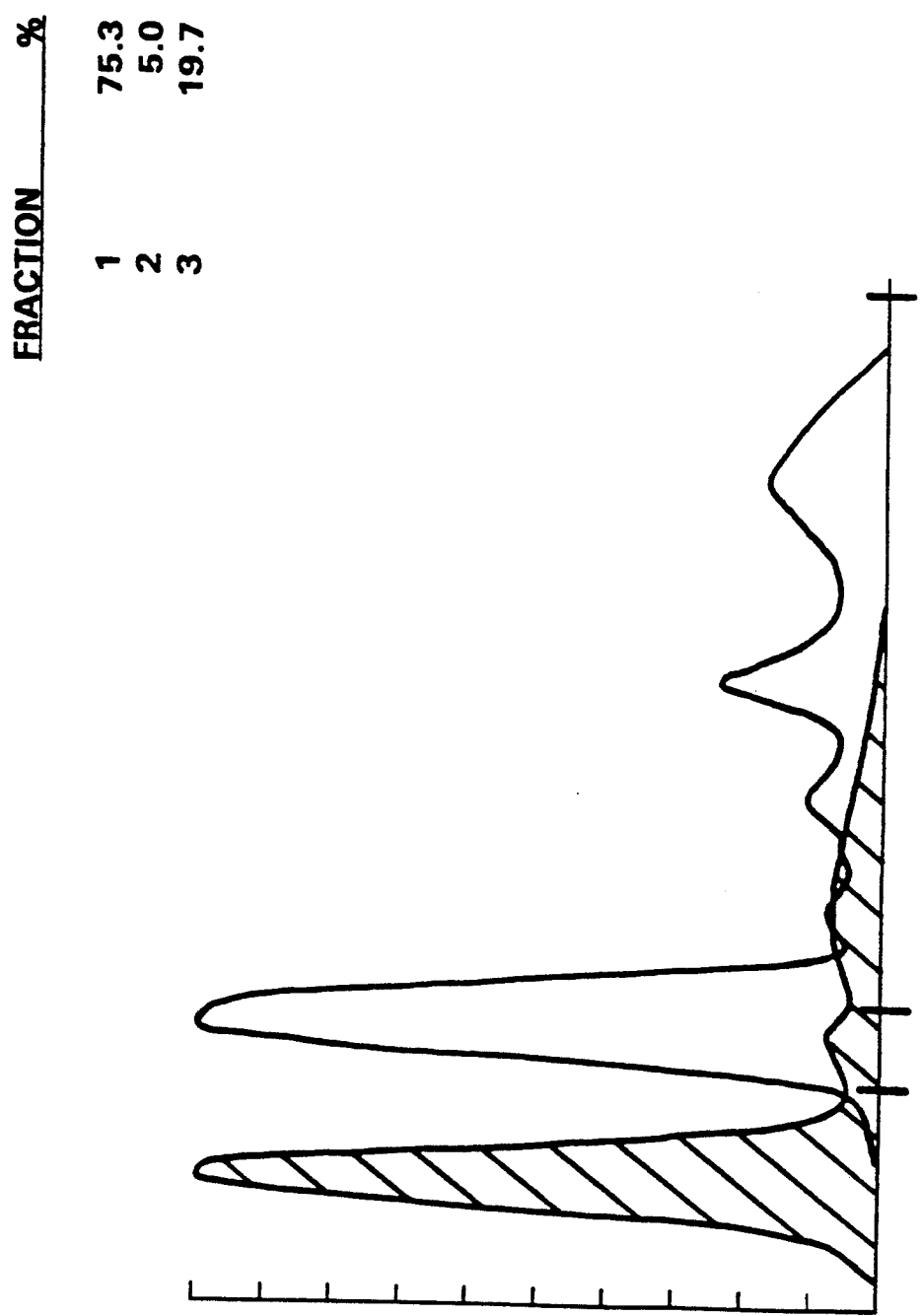
FIG. 6 shows an overlay of protein electrophoresis of prealbumin prepared by the Raz method, onto normal human serum pattern.

This prealbumin was found to be only 75% pure by protein electrophoresis. See FIG. 5. When compared to the electrophoretic pattern of normal serum the contaminating proteins are observed in the albumin, and alpha globulin regions. See FIG. 6.

The purified prealbumin has been monitored for stability while being stored refrigerated and frozen. The prealbumin has been tested for quantity by radial immunodiffusion and purity by protein electrophoresis. After ten months storage at these conditions, the prealbumin has remained stable.

TABLE II

STABILITY OF PREALBUMIN

| MONTHS | |
|---|---|
| | STORAGE AT 2–8° C. |
| 0 | 7395 mg of prealbumin/liter of solution |
| 4 | 7020 mg of prealbumin/liter of solution |
| 6 | 7879 mg of prealbumin/liter of solution |
| 10 | 7005 mg of prealbumin/liter of solution |
| | STORAGE AT −20° C. |
| 0 | N/A |
| 4 | N/A |
| 6 | 7724 mg of prealbumin/liter of solution |
| 10 | 7275 mg of prealbumin/liter of solution |

EXAMPLE 2

Preparation of Cerebrospinal Fluid Control

A clean container with a stirring device is prepared. 800 mL of distilled is placed into the container. While mixing, the following chemicals are added:

| Constituents | Level I | Level II |
|---|---|---|
| HEPES (N-2-hydroxyethyl piperazine-$N_2'$-2-ethane sulfonic acid) | 12.3 gm | 9.2 gm |
| Sodium HEPES | 9.4 gm | 7.0 gm |
| Sodium Cloride | 6.6 gm | 5.3 gm |
| Potassium Cloride | 0.19 gm | 0.3 gm |
| Glucose | 0.57 gm | 0.33 gm |
| Sodium Lactate | 0.38 gm | 1.5 gm |
| Human Serum | 0.29 gm | 0.63 gm |
| Prealbumin | 10.0 mg | 15.0 mg |
| Sodium Azide 25% | 0.8 mL | 0.8 mL |

After all chemicals are dissolved, the total volume of the solution is brought to one liter with distilled water. All constituents are analyzed and adjusted within the above described specifications. A gas cylinder of oxygen is connected to a two stage regulator. Rubber tubing or equivalent is connected to the regulator and to the batching container. The first stage of the regulator is opened. The second stage is slowly opened until the gas flow through the solution is approximately 0.4 SCFH (square cubic feet per hour). While mixing, the pool is flushed in this manner at room temperature.

After flushing, a sample of the solution is removed and concentrated approximately 60 times. This concentrated sample is then evaluated by serum protein electrophoresis. If the electrophoretic pattern does not show a single peak in the prealbumin region, reflushing is necessary.

After a normal electrophoretic pattern is recovered, the solution is sterile filtered through 0.22 micron membranes into sterilized containers. The sterile solution is then filled into sterilized vials at three mL each.

These cerebrospinal fluid controls were evaluated for stability according to a protocol for the evaluation of the stability of diagnostics products. This protocol states guidelines for accelerated stability studies. According to this protocol, a product that is stored at 37° C. for one week is stable for one year at 2°–8° C. Accelerated stability studies were used to determine the performance characteristics of the product under storage conditions which stress the product in comparison to those recommended for use and handling of the product. The cerebrospinal fluid controls were analyzed after storage at 25° C. for three months and 37° C. for four weeks. Results from these analyses show the product to be stable and therefore have a predicted shelf life of greater than three years. The product has been monitored at 2°–8° C. for greater than one year. See Table III.

TABLE III

STABILITY OF CEREBROSPINAL FLUID CONTROL

| CONSTITUENTS | UNITS | 2–8° C. Storage | 25° C. Storage | 37° C. Storage |
|---|---|---|---|---|
| LEVEL I | | | | |
| PROTEIN | mg/dL | 28 | 30 | 28 |
| LACTIC ACID | mM | 1.2 | 1.1 | 1.2 |
| GLUCOSE | mg/dL | 56 | 56 | 56 |
| CHLORIDE | mM | 120 | 127 | 122 |
| SODIUM | mM | 149 | 150 | 149 |
| POTASSIUM | mM | 2.6 | 2.6 | 2.6 |
| IgA | mg/dL | 1.2 | 1.1 | 1.3 |
| IgG | mg/dL | 4.6 | 5.0 | 4.3 |
| IgM | mg/dL | 1.2 | 1.6 | 1.4 |
| ELECTROPHORESIS: | | | | |
| PRE-ALBUMIN | % OF TOTAL | 6.2 | 6.2 | 5.2 |
| ALBUMIN | % OF TOTAL | 66 | 65 | 66 |
| ALPHA 1 | % OF TOTAL | 3.2 | 3.0 | 3.7 |
| ALPHA 2 | % OF TOTAL | 6.3 | 6.3 | 6.2 |
| BETA | % OF TOTAL | 7.7 | 8.2 | 8.2 |
| GAMMA | % OF TOTAL | 10.5 | 11.2 | 11.6 |
| LEVEL II | | | | |
| PROTEIN | mg/dL | 61 | 66 | 64 |
| LACTIC ACID | mM | 7.6 | 7.7 | 7.6 |
| GLUCOSE | mg/dL | 31 | 34 | 33 |
| CHLORIDE | mM | 102 | 106 | 102 |
| SODIUM | mM | 127 | 127 | 127 |
| POTASSIUM | mM | 4.1 | 4.2 | 4.1 |
| IgA | mg/dL | 2.5 | 2.5 | 3.0 |
| IgG | mg/dL | 10.2 | 10.4 | 10.3 |
| IgM | mg/dL | 1.9 | 2.4 | 1.9 |
| ELECTROPHORESIS: | | | | |
| PRE-ALBUMIN | OF TOTAL | 5.4 | 4.9 | 4.6 |
| ALBUMIN | % OF TOTAL | 63 | 63 | 62 |
| ALPHA 1 | % OF TOTAL | 2.8 | 2.4 | 2.7 |
| ALPHA 2 | % OF TOTAL | 7.4 | 7.6 | 7.8 |
| BETA | % OF TOTAL | 8.6 | 9.6 | 9.6 |
| GAMMA | % OF TOTAL | 12.5 | 12.6 | 13.5 |

The cerebrospinal fluid controls were also evaluated for open vial stability. Vials were tested after being open for two weeks. Analyses of the opened vials showed no change when compared to vials that were freshly sampled. See TABLE IV.

TABLE IV

| CONSTITUENT | UNITS | FRESH VIAL | OPEN 14 DAYS |
|---|---|---|---|
| OPEN VIAL STABILITY LEVEL I | | | |
| Protein | mg/dL | 25.5 | 25.7 |
| Glucose | mg/dL | 60.0 | 60.2 |
| Sodium | mM | 158 | 158 |
| Chloride | mM | 113 | 112 |

TABLE IV-continued

| CONSTITUENT | UNITS | FRESH VIAL | OPEN 14 DAYS |
|---|---|---|---|
| IgG | mg/dL | 4.98 | 4.99 |
| IgA | mg/dL | 1.18 | 1.16 |
| IgM | mg/dL | <0.69 | <0.69 |
| ELECTROPHORESIS: | | | |
| Prealbumin | % of Total | 3.6 | 4.4 |
| Albumin | % of Total | 65 | 64 |
| Alpha 1 | % of Total | 3.0 | 3.6 |
| Alpha 2 | % of Total | 6.8 | 7.1 |
| Beta | % of Total | 9.2 | 9.2 |
| Gamma | % of Total | 11.9 | 12.1 |
| OPEN VIAL STABILITY LEVEL II | | | |
| Protein | mg/dL | 59.5 | 59.1 |
| Glucose | mg/dL | 33.3 | 33.2 |
| Sodium | mM | 127 | 127 |
| Chloride | mM | 96 | 97 |
| IgG | mg/dL | 11 | 11 |
| IgA | mg/dL | 2.59 | 2.58 |
| IgM | mg/dL | 0.89 | 0.91 |
| ELECTROPHORESIS: | | | |
| Prealbumin | % of Total | 2.5 | 2.6 |
| Albumin | % of Total | 61 | 62 |
| Alpha 1 | % of Total | 4.0 | 4.1 |
| Alpha 2 | % of Total | 8.5 | 7.8 |
| Beta | % of Total | 10.0 | 9.5 |
| Gamma | % of Total | 13.5 | 13.8 |

EXAMPLE 3

The cerebrospinal fluid control prepared in Example 2 was used as a control in several diagnostic tests. The results of these assays are reported in TABLE V.

TABLE V

METHODS COMPARISON

| CONSTITUENT | UNITS | METHOD | LEVEL I | LEVEL II |
|---|---|---|---|---|
| Protein | mg/dL | DuPont aca 4 | 28.5 | 59.8 |
| | mg/dL | DuPont aca 3 | 22 | 57 |
| | mg/dL | Kodak Ektachem | 25.6 | 75.6 |
| | mg/dL | Abbott Spectrum | 28.6 | 60.2 |
| Lactic Acid | mM | DuPont aca 3 | 1.2 | 7.0 |
| | mM | Baxter Paramax | 1.4 | 7.1 |
| Glucose | mg/dL | DuPont aca 4 | 57.2 | 33.5 |
| | mg/dL | DuPont aca 3 | 57 | 33.8 |
| | mg/dL | DuPont Dimension | 56.6 | 33.4 |
| | mg/dL | Kodak Ektachem | 60.1 | 35.9 |
| | mg/dL | Abbott Spectrum | 58.5 | 35.4 |
| | mg/dL | Baxter Paramax | 60.0 | 36.0 |
| Chloride | mM | DuPont aca 3 | 122 | 104 |
| | mM | Kodak Ektachem | 112 | 93 |
| | mM | Abbott Spectrum | 119 | 101 |
| | mM | DuPont Dimension | 114 | 97 |
| | mM | NOVA Biomedical | 119 | 101 |
| | mM | Baxter Paramax | 113 | 95 |
| Sodium | mM | Abbott Spectrum | 152 | 130 |
| | mM | DuPont Dimension | 153 | 128 |
| | mM | NOVA Biomedical | 150 | 126 |
| Potassium | mM | NOVA Biomedical | 2.7 | 4.1 |
| IgG | mg/dL | RID | 8.0 | 16 |
| | mg/dL | Beckman Array | 5.0 | 11 |
| IgA | mg/dL | RID | 1.4 | 3.0 |
| | mg/dL | Beckman Array | 1.2 | 2.6 |
| IgM | mg/dL | RID | 1.4 | 1.9 |
| | mg/dL | Beckman Array | <0.69 | 0.91 |
| ELECTROPHORESIS: % OF TOTAL HELENA | | | | |
| Prealbumin | | | 7.0 | 5.5 |
| Albumin | | | 63 | 61 |
| Alpha 1 | | | 3.8 | 3.9 |
| Alpha 2 | | | 6.4 | 7.4 |
| Beta | | | 7.3 | 8.3 |
| Gamma | | | 13.0 | 14.0 |
| BECKMAN PARAGON | | | | |
| Prealbumin | | | 5.5 | 3.5 |
| Albumin | | | 66 | 67 |
| Alpha 1 | | | 3.7 | 3.7 |
| Alpha 2 | | | 6.6 | 7.1 |
| Beta | | | 7.6 | 7.6 |
| Gamma | | | 10.0 | 11.0 |

We claim:

1. An electrophoretic method to assess human cerebrospinal fluid comprising:
   a) preparing a stable liquid human based cerebrospinal fluid control, wherein the control is made by the process comprising:
      (i) combining a sufficient amount of lactic acid, chloride, glucose, serum, purified prealbumin, and potassium in a buffer to simulate normal human cerebrospinal fluid;
      (ii) gassing said fluid with oxygen to obtain normal electrophoretic patter for human cerebrospinal fluid; and
      (iii) filtering said fluids to remove all microbial contaminants;
   b. obtaining an electrophoretic pattern of said control and a sample human cerebrospinal fluid; and
   c. comparing the electrophoretic pattern of the control with the electrophoretic pattern of the sample.

2. The method of claim 1 wherein the electrophoretic patterns of the sample and control are obtained simultaneously.

* * * * *